United States Patent
Nishino et al.

(10) Patent No.: US 8,182,147 B2
(45) Date of Patent: May 22, 2012

(54) PORTABLE RADIOGRAPHIC IMAGING DEVICE AND RADIOGRAPHIC IMAGING SYSTEM

(75) Inventors: Naoyuki Nishino, Kanagawa (JP); Keiji Tsubota, Kanagawa (JP); Yasunori Ohta, Kanagawa (JP); Yutaka Yoshida, Kanagawa (JP); Takashi Shoji, Kanagawa (JP); Kiyoshi Kondou, Kanagawa (JP); Yuji Kurachi, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 285 days.

(21) Appl. No.: 12/626,697

(22) Filed: Nov. 27, 2009

(65) Prior Publication Data

US 2010/0135464 A1 Jun. 3, 2010

(30) Foreign Application Priority Data

Dec. 1, 2008 (JP) .................................. 2008-306560

(51) Int. Cl.
*H01J 31/49* (2006.01)
(52) U.S. Cl. ....................................................... 378/189
(58) Field of Classification Search .................... 378/62, 378/116–117, 98.8, 189, 198
See application file for complete search history.

(56) References Cited

U.S. PATENT DOCUMENTS

2006/0120512 A1* 6/2006 Watanabe ..................... 378/198

FOREIGN PATENT DOCUMENTS

| JP | 2005-211226 A | 8/2005 |
| JP | 2006-158508 A | 6/2006 |
| JP | 2007-082907 A | 4/2007 |

* cited by examiner

*Primary Examiner* — Courtney Thomas
(74) *Attorney, Agent, or Firm* — Solaris Intellectual Property Group, PLLC

(57) ABSTRACT

A portable radiographic imaging device includes an operation unit, a controller, and an execution unit. The operation unit is operated when a target function is selected from plural different functions relating to radiographic image capturing. When a first condition, that expresses that a predetermined region has been placed at a predetermined placement portion, is established, the controller carries out control such that a function that should be effective when the first condition is established is selected. When a second condition, that expresses that the predetermined region is not placed at the placement portion, is established, the controller carries out control such that a function that should be effective when the second condition is established is selected. When the operation unit is operated, the execution unit executes a function that is controlled by the controller to be selected.

5 Claims, 13 Drawing Sheets

PORTABLE RADIOGRAPHIC IMAGING DEVICE AND RADIOGRAPHIC IMAGING SYSTEM

CROSS-REFERENCE TO RELATED APPLICATION

This application claims priority under 35 USC 119 from Japanese Patent Application No. 2008-306560 filed on Dec. 1, 2008, the disclosure of which is incorporated by reference herein.

BACKGROUND OF THE INVENTION

1. Field of the Invention

The present invention relates to a portable radiographic imaging device and a radiographic imaging system.

2. Description of the Related Art

FPDs (flat panel detectors), in which a radiation-sensitive layer is disposed on a TFT (thin film transistor) active matrix substrate and that can convert radiation directly into digital data, have been put into practice in recent years. Portable radiographic imaging devices (hereinafter also called "electronic cassettes"), that carry out image capturing by generating image information expressing a radiographic image manifested by irradiated radiation and storing the generated image information in a predetermined storage region by using an FPD or the like, have been put into practice.

This type of electronic cassette is equipped with an operation unit that is formed by switches and keys or by a touch panel or the like and that receives input operations for controlling the FPD and other electronic equipment packaged in the electronic cassette. However, when the electronic cassette is mounted to an imaging stand, there is the concern that erroneous working will be carried out due to the operation unit being operated erroneously.

As a technique that prevents erroneous operation of an electronic cassette, Japanese Patent Application Laid-Open (JP-A) No. 2006-158508 discloses a technique that, when an electronic cassette having a screen switching key is in a state of being moved, erroneous operation during the movement is prevented by rendering the screen switching key unusable. JP-A No. 2005-211226 discloses a technique relating to operability at the time when an electronic cassette is mounted to an imaging stand.

The techniques of aforementioned cannot prevent erroneous working due to erroneous operation with respect to an electronic cassette when the electronic cassette is placed at an imaging stand.

There are provided a portable radiographic imaging device and a radiographic imaging system that can prevent erroneous working due to erroneous operation when a predetermined region is placed at a predetermined placement portion.

SUMMARY OF THE INVENTION

The present invention has been made in view of the above circumstances and provides a portable radiographic imaging device and a radiographic imaging system.

According to an aspect of the invention, there is provided a portable radiographic imaging device including: an operation unit operated when selecting a target function from a plurality of different functions relating to radiographic image capturing; a controller that, when a first condition, that expresses that a predetermined region has been placed at a predetermined placement portion, is established, carries out control such that a function that should be effective when the first condition is established is selected, and, when a second condition, that expresses that the predetermined region is not placed at the placement portion, is established, carries out control such that a function that should be effective when the second condition is established is selected; and an execution unit that, when the operation unit is operated, executes a function that is controlled by the controller to be selected.

BRIEF DESCRIPTION OF THE DRAWINGS

Preferred embodiments of the present invention will be described in detail based on the following figures, wherein.

DETAILED DESCRIPTION OF THE INVENTION

Figure 1:
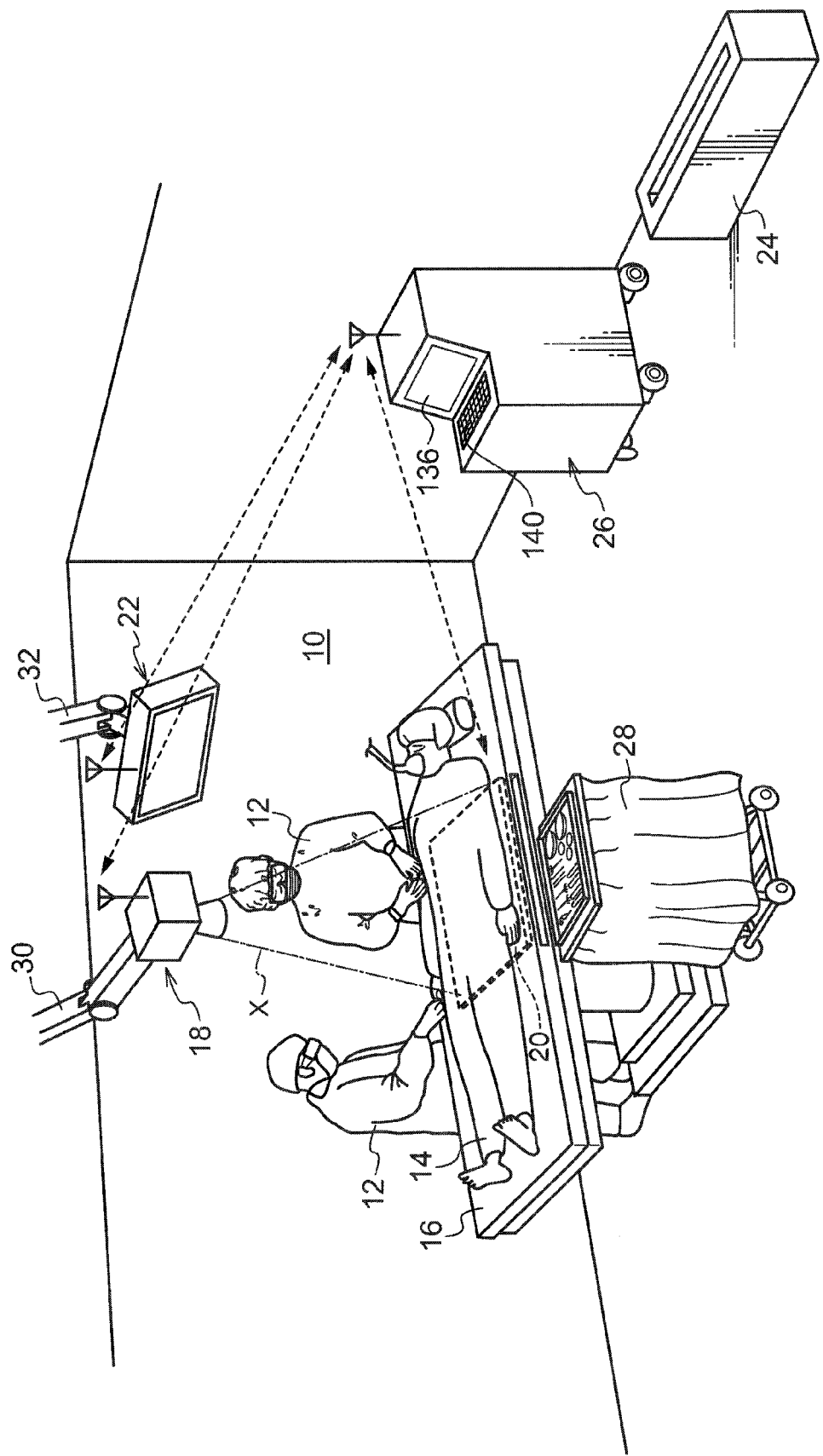
FIG. 1 is a drawing showing the situation in an operating room in which an imaging system relating to an exemplary embodiment is set.

Hereinafter, preferred exemplary embodiments for implementing the present invention will be described in detail with reference to the drawings.

First Exemplary Embodiment

The structure of a radiographic imaging system 10 (hereinafter also called "imaging system 10") relating to the present exemplary embodiment will be described. A situation in which the imaging system 10 is set within an operating room is illustrated in FIG. 1 as an example of a situation of disposing the imaging system 10 relating to the present exemplary embodiment.

The imaging system 10 is for carrying out capturing of radiographic images in accordance with operations of a doctor 12 or a radiology technician. The imaging system 10 has an operating table 16 on which a patient 14 is placed, a radiation irradiating device 18 that irradiates, onto the patient 14, radiation X formed of a radiation amount according to image capturing conditions, an electronic cassette 20 that carries out image capturing by detecting the radiation X that has been transmitted through the patient 14 and storing image information, that expresses a radiographic image corresponding to the detected radiation amount, in a predetermined storage region, a display device 22 that displays the radiographic image obtained by image capturing at the electronic cassette 20, a cradle 24 that charges a battery 44 (see FIG. 2) incorporated in the electronic cassette 20, and a console 26 that controls the radiation irradiating device 18, the electronic cassette 20 and the display device 22. In the imaging system 10 relating to the present exemplary embodiment, wireless communication by radio waves is carried out between, on the one hand, the radiation irradiating device 18, the electronic cassette 20 and the display device 22, and, on the other hand, the console 26. However, the present invention is not limited to the same, and optical wireless communication using infrared rays or the like may be carried out.

In the operating room shown in FIG. 1, in addition to the imaging system 10, an instrument table 28, on which various types of instruments that the doctor 12 uses in surgery are placed, is disposed at the side of the operating table 16. Various devices that are needed in surgery such as anesthesia equipment, suction equipment, an electrocardiograph, a blood pressure meter, and the like are disposed around the operating table 16 (these devices are omitted in FIG. 1).

The radiation irradiating device 18 is connected to a universal arm 30, and can be moved to a desired position that corresponds to the region to be imaged of the patient 14, and can be withdrawn to a position at which it does not get in the way of the surgery performed by the doctor 12. The display device 22 is connected to a universal arm 32, and can be moved to a position at which the doctor 12 can easily confirm the captured radiographic image.

Figure 2:
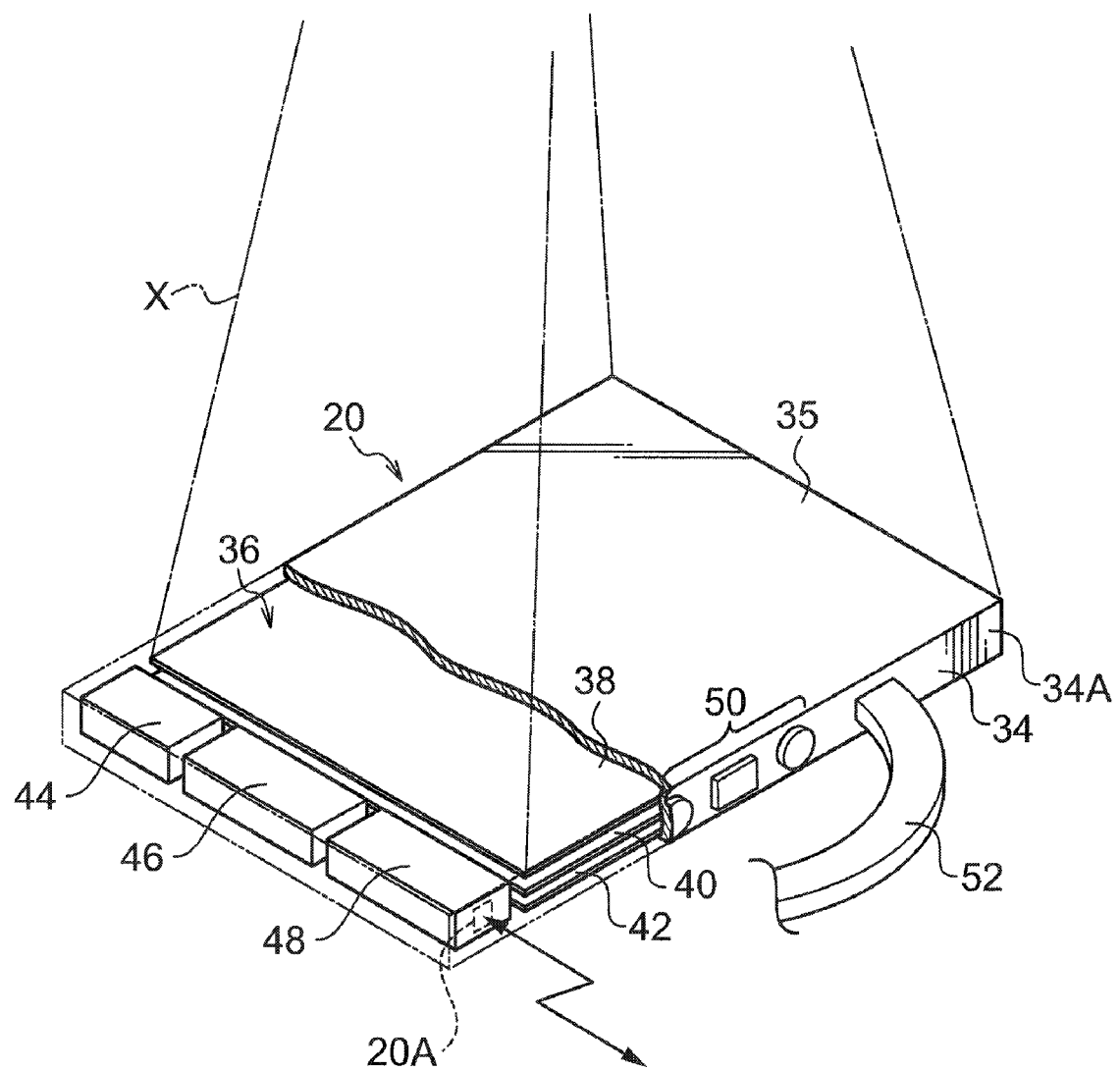
FIG. 2 is a broken perspective view showing the structure of an electronic cassette relating to a first exemplary embodiment.

A broken perspective view showing the structure of the electronic cassette 20 relating to the first exemplary embodiment is shown in FIG. 2.

As shown in FIG. 2, the electronic cassette 20 has a housing 34 formed from a material through which the radiation X is transmitted. An imaging device 36 is housed within the housing 34. A grid 38 that removes the scattered radiation of the radiation X due to the patient 14, a radiation detector 40 that detects the radiation X that has been transmitted through the patient 14, and a lead plate 42 that absorbs the back-scattered radiation of the radiation X, are disposed in that order from an irradiating surface 35 side of the housing 34 onto which the radiation X is irradiated, as members that structure the imaging device 36. The imaging device 36 has the battery 44 that is the power supply of the electronic cassette 20, an electronic cassette controller 46 that drives and controls the radiation detector 40 by electric power supplied from the battery 44, and a transmitter/receiver 48 that transmits and receives, to and from the console 26, signals including information of the radiation X detected by the radiation detector 40.

An operation unit 50, that is operated at the time of selecting the function that is the object from among the plural different functions relating to radiographic image capturing, is provided at one surface side 34A of the housing 34. Examples of operation unit 50 include a power switch that switches the power supply on/off, an instruction key that instructs transmission of image information to the console 26, and a mode selection switch that switches between an image capturable mode, that sets the electronic cassette 20 in a state in which images can be captured, and a maintenance mode, that sets the electronic cassette 20 in a state in which maintenance can be carried out thereon. The aforementioned "plural different functions" include a function that renders control by operation with respect to the operation unit 50 ineffective, and a function that renders control by operation with respect to the operation unit 50 effective.

A semi-annular grasping portion 52, whose both ends are fixed to the one side surface 34A, is provided at the one side surface 34A of the housing 34 so as to straddle the operation unit 50. The grasping unit 52 is structured so as to be able to be grasped by a user catching his/her fingers thereon.

Figure 3:
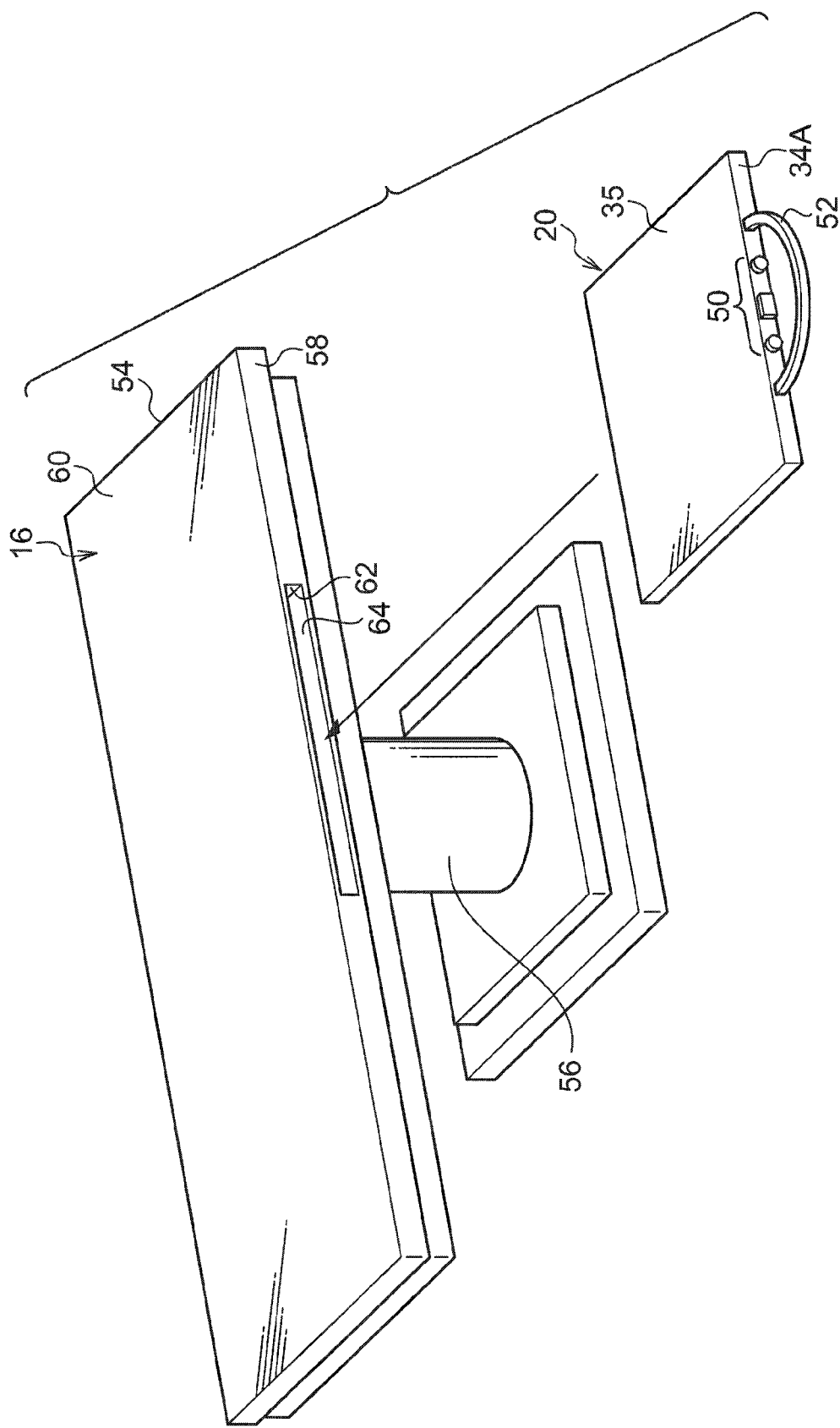
FIG. 3 is a perspective view showing the external appearance of an operating table and the electronic cassette relating to the first exemplary embodiment.

FIG. 3 is a perspective view showing the external appearance of the operating table 16 and the electronic cassette 20 relating to the first exemplary embodiment.

As shown in FIG. 3, the operating table 16 is structured of a material through which the radiation X is transmitted, and has a placement portion 54 that is substantially shaped as a rectangular flat plate and on which the patient 14 is placed, and a leg portion 56 that stands erect at the center of the bottom surface of the placement portion 54 and supports the placement portion 54.

An opening 62 is formed in a portion of one side surface 58 of the placement portion 54. An accommodating portion 64, in which the electronic cassette 20 is accommodated via the opening 62 such that the irradiating surface 35 of the electronic cassette 20 is substantially parallel to a top surface 60 of the placement portion 54, is formed in the placement portion 54.

Figure 4:
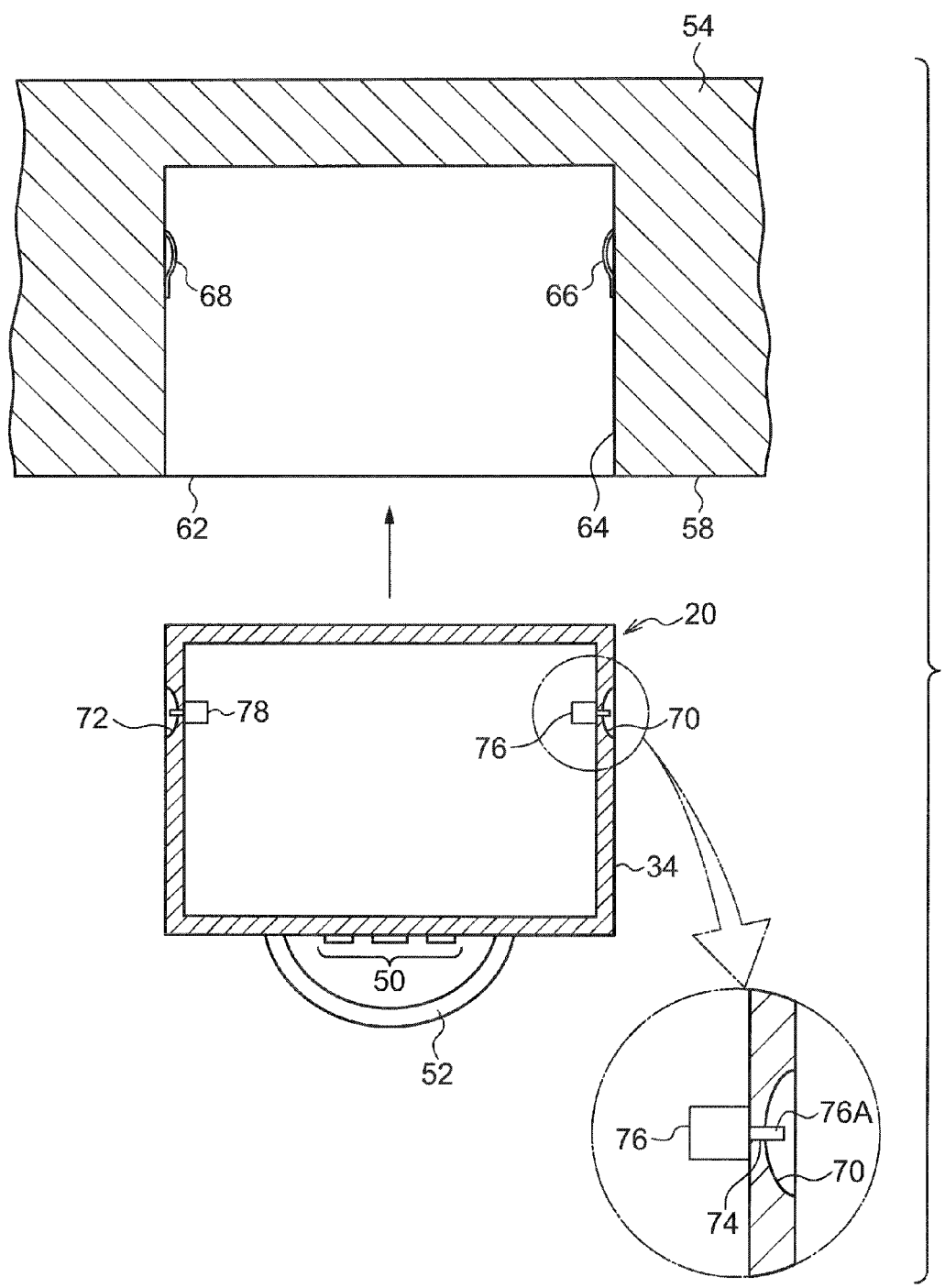
FIG. 4 is a cross-sectional view showing the structure of a placement portion and a housing of the electronic cassette relating to the first exemplary embodiment.

A cross-sectional view showing the structures of the placement portion 54 and the housing 34 of the electronic cassette 20 relating to the present exemplary embodiment is shown in FIG. 4.

As shown in FIG. 4, semi-annular plate springs 66, 68, whose one ends are fixed to wall surfaces and whose other ends contact the wall surfaces, are provided so as to oppose one another at the respective side walls of the accommodating portion 64 of the placement portion 54. Grooves 70, 72, with which the plate springs 66, 68 respectively fit-together when the electronic cassette 20 is accommodated in the accommodating portion 64, are formed at the housing 34 of the electronic cassette 20. Through-holes 74 are formed at the bottoms of the grooves 70, 72. Microswitches 76, 78 are fixed to the inner walls of the housing 34 so as to correspond to the grooves 70, 72.

The structures of the microswitches 76, 78 will be described. Note that, because the microswitches 76, 78 have the same structures, description will be given by using the microswitch 76 as an example.

The microswitch 76 has a push portion 76A that is urged to project outward by an incorporated return spring. The push portion 76A is inserted through the through-hole 74, and projects-out from the bottom of the groove 70. The microswitch 76 is turned on by the push portion 76A being pushed against the urging force of the return spring.

When the electronic cassette 20 is inserted into the accommodating portion 64 via the opening 62, the plate spring 66 fits-together with the groove 70 in due course, the push portion 76A is pushed by the plate spring 66, the microswitch 76 is turned on, and the electronic cassette 20 is held at a predetermined position of the accommodating portion 64. When the grasping portion 52 is grasped and force is applied so as to pull the electronic cassette 20 out from the accommodating portion 64, the plate spring 66 comes-out from the groove 70 while elastically deforming, the microswitch 76 is turned off, and the electronic cassette 20 is removed from the predetermined position of the accommodating portion 64.

Figure 5:
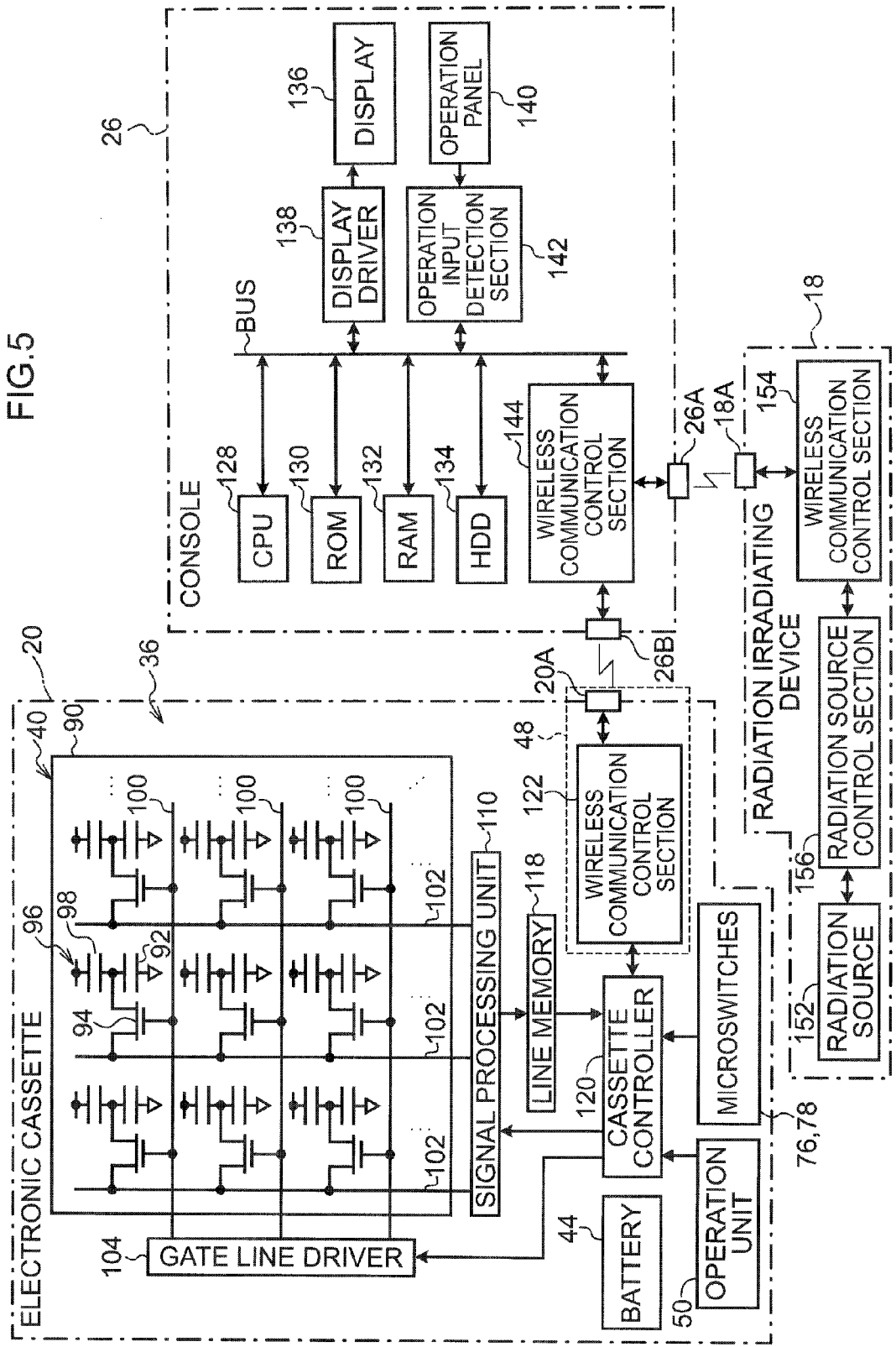
FIG. 5 is a block diagram showing the structure of main portions of the imaging systems relating to the exemplary embodiment.

A block diagram showing the structure of main portions of the imaging system 10 relating to the present exemplary embodiment is shown in FIG. 5.

Figure 6:
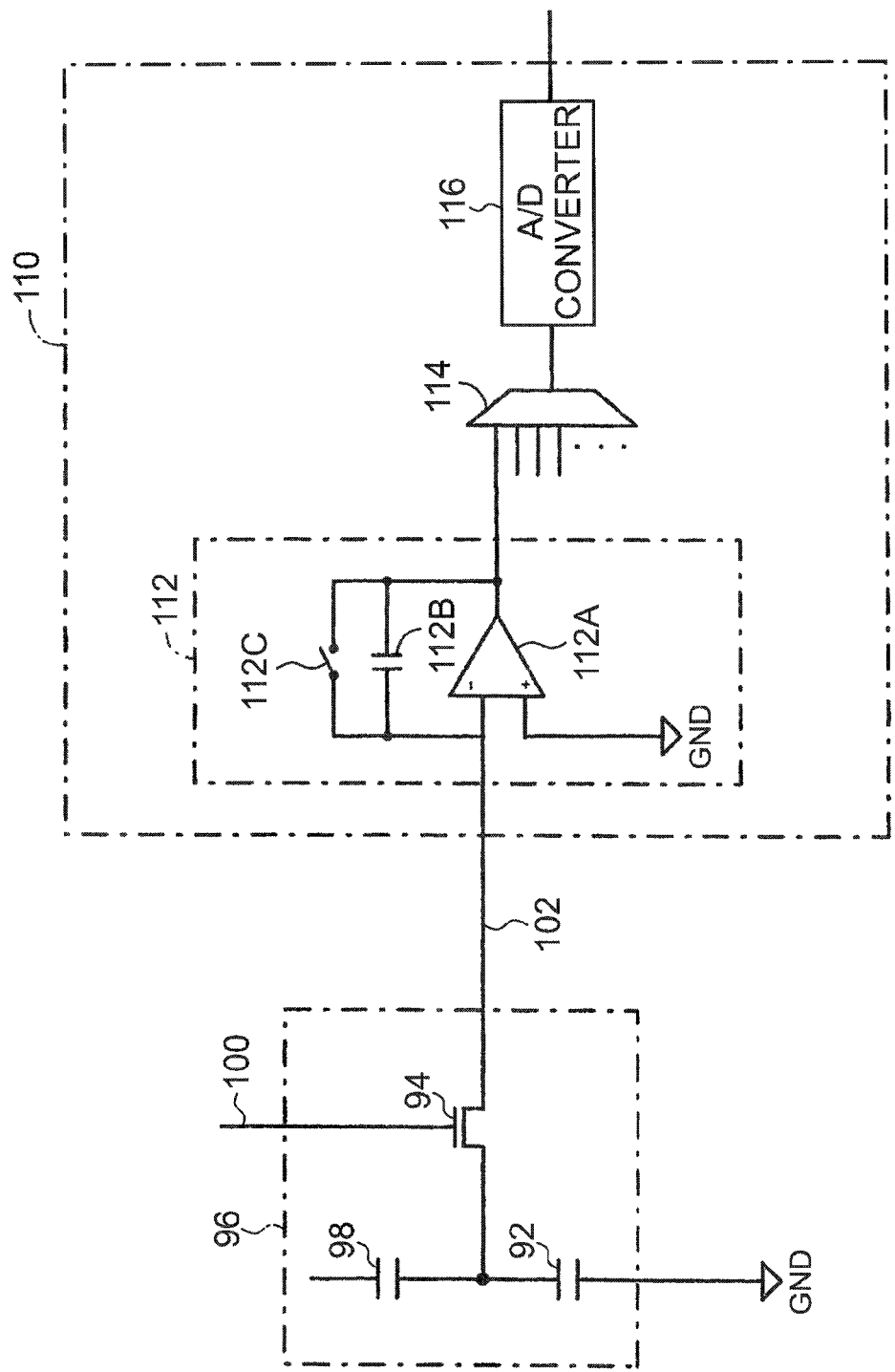
FIG. 6 is an equivalent circuit diagram focusing on one pixel portion of a radiation detector relating to the exemplary embodiment.

An equivalent circuit diagram focusing on one pixel portion of the radiation detector 40 relating to the present exemplary embodiment is shown in FIG. 6.

As shown in FIG. 6, the source of the TFT 94 is connected to the data line 102, and the data line 102 is connected to the signal processing unit 110. The drain of the TFT 94 is connected to the storage capacitor 92 and the photoelectric converting portion 98, and the gate of the TFT 94 is connected to the gate line 100.

The signal processing unit 110 has a sample-and-hold circuit 112 for each of the individual data lines 102. The charge signals transmitted from the individual data lines 102 are held in the sample-and-hold circuits 112. The sample-and-hold circuit 112 is structured to include an operational amplifier 112A and a capacitor 112B, and converts the charge signal into analog voltage. A switch 112C, that serves as a resetting circuit that shorts both electrodes of the capacitor 112B and discharges the charges accumulated in the capacitor 112B, is provided at the sample-and-hold circuit 112.

A multiplexer 114 and an A/D converter 116 are connected in that order to the output sides of the sample-and-hold circuits 112. The charge signals held in the individual sample-and-hold circuits are converted into analog voltages, are inputted in order (serially) to the multiplexer 114, and are converted into digital image information by the A/D converter 116.

A line memory 118 is connected to the signal processing unit 110 (see FIG. 5). The image information outputted from the A/D converter 116 of the signal processing unit 110 is stored in order in the line memory 118. The line memory 118 has a storage capacity that can store a predetermined number of lines of image information expressing a radiographic image. Each time reading-out of the charges of one line is carried out line-by-line, the image information of the read-out one line is successively stored in the line memory 118.

The line memory 118 is connected to a cassette controller 120 that controls the overall operation of the electronic cassette 20. The cassette controller 120 is realized by a microcomputer, and a wireless communication controller 122 is connected thereto. The wireless communication controller 122 is connected to an antenna 20A, and carries out control of the transfer of various types of information between the electronic cassette 20 and an external device via the antenna 20A.

The microswitches 76, 78 are connected to the cassette controller 120. Accordingly, the cassette controller 120 can know of the on/off states of the microswitches 76, 78.

The operation unit 50 is connected to the cassette controller 120. Accordingly, the cassette controller 120 can know the state of the operation of the operation unit 50 by the user.

The electronic cassette 20 has the battery 44 that is a chargeable secondary battery. The above-described various types of circuits and respective elements (the gate line driver 104, the signal processing unit 110, the line memory 118, the wireless communication controller 122, and the microcomputer that functions as the cassette controller 120) are operated by electric power supplied from the battery 44.

The console 26 is structured as a server computer, and has a display 136 (refer to FIG. 1 as well), that displays operation menus, captured radiographic images and the like, and an operation panel 140 (refer to FIG. 1 as well) that is structured to include plural keys and by which various types of information and operating instructions are inputted.

The console 26 includes: a CPU 128 that governs the operations of the overall device; a ROM 130 in which various types of programs including control programs and the like are stored in advance; a RAM 132 that temporarily stores various types of data; an HDD (hard disk drive) 134 that stores and holds various types of data; a display driver 138 that controls the display of various types of information on the display 136; an operation input detection section 142 that detects the operated state of the operation panel 140; and a wireless communication controller 144 that is connected to an antenna 26A and carries out wireless communication of various types of information, such as exposure conditions and state information of the radiation irradiating device 18 and the like, with the radiation irradiating device 18 via the antenna 26A, and is connected to an antenna 26B and carries out wireless communication of various types of information, such as image information and the like, with the electronic cassette 20 via the antenna 26B.

The CPU 128, the ROM 130, the RAM 132, the HDD 134, the display driver 138, the operation input detection section 142, and the wireless communication controller 144 are connected to one another via a system bus BUS. Accordingly, the CPU 128 can access the ROM 130, the RAM 132 and the HDD 134, and can carry out control of display of various types of information on the display 136 via the display driver 138, learning of the operational state of the operation panel 140 by the user via the operation input detection section 142, and control of transmission and reception of various types of information with the radiation irradiating device 18 and the electronic cassette 20 via the wireless communication controller 144.

The radiation irradiating device 18 has a radiation source 152 that outputs the radiation X, a wireless communication controller 154 that is connected to an antenna 18A and carries out wireless communication of various types of information, such as exposure conditions and state information of the radiation radiating device 18 and the like, with the console 26 via the antenna 18A, and a radiation source controller 156 that controls the radiation source 152 on the basis of received exposure conditions. The radiation source controller 156 as well is realized by a microcomputer, and stores received exposure conditions, and causes the radiation X to be irradiated from the radiation source 152 on the basis of stored exposure conditions.

Figure 7:
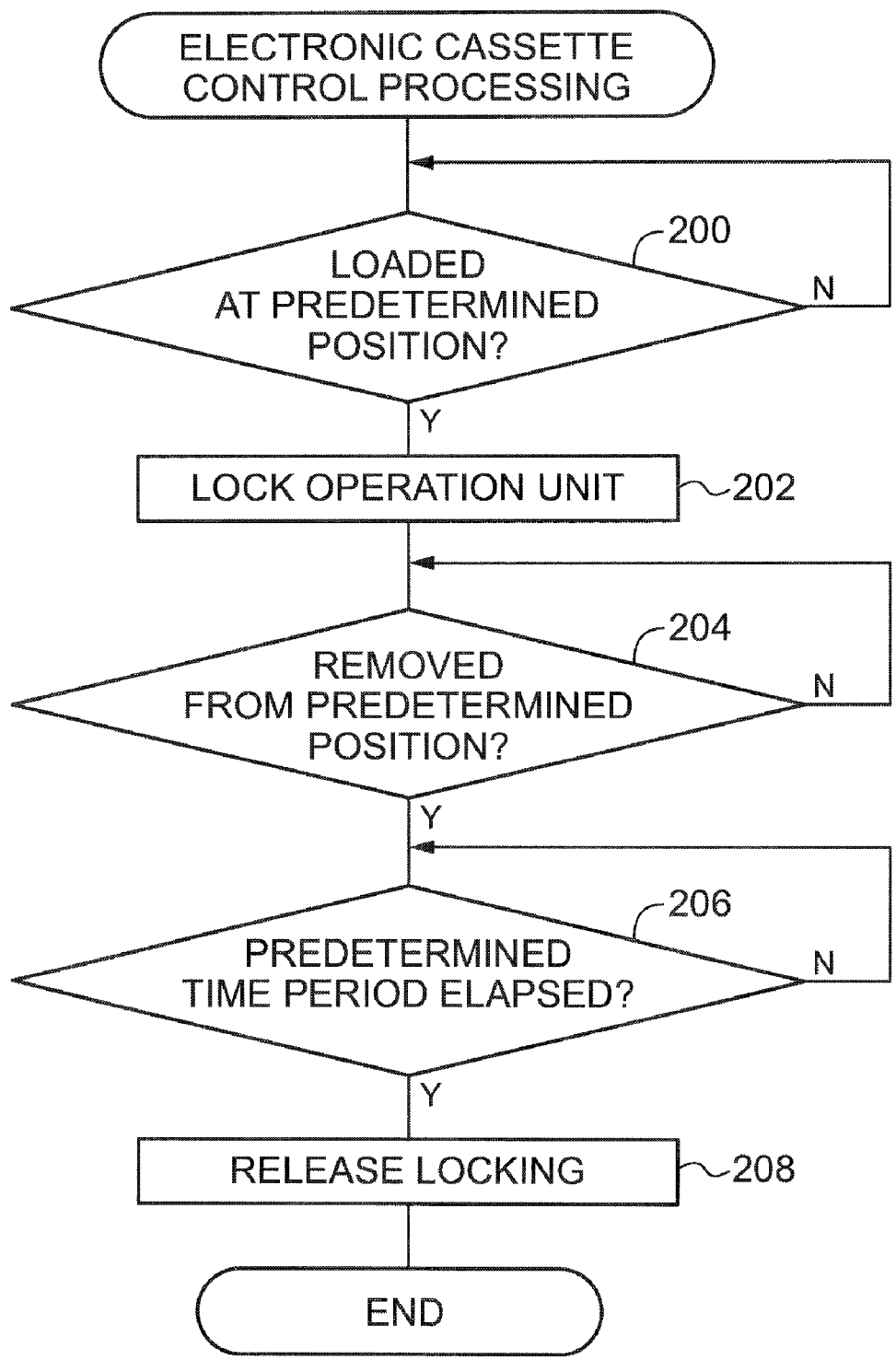
FIG. 7 is a flowchart showing the flow of processings of an electronic cassette control processing program relating to the first exemplary embodiment.

A processing routine of the electronic cassette 20 at the time when the power supply of the electronic cassette 20 is turned on will be described with reference to FIG. 7. FIG. 7 is a flowchart showing the flow of processings of an electronic cassette control processing program that is executed by the cassette controller 120 of the electronic cassette 20 at this time. This program is stored in advance in a predetermined region of a memory that is contained in the microcomputer that realizes the cassette controller 120.

In step 200 of FIG. 7, the routine stands-by until the electronic cassette 20 is loaded at the predetermined position of the accommodating portion 64. In the electronic cassette 20 relating to the present exemplary embodiment, the processing of standing-by until the microswitches 76, 78 are turned on is applied as the processing of present step 200, but the present invention is not limited to the same. For example, reflection-type photosensors may be used instead of the microswitches 76, 78, and processing for standing-by until these reflection-type photosensors are turned on may be applied as the processing of step 200. In this case, for example, a form may be used in which, instead of the plate springs 66, 68, reflecting plates are provided at the positions of the plate springs 66, 68, and the lights emitted from the reflection-type photosensors are reflected at the reflecting plates, and the reflected lights are received by the reflection-type photosensors. In this way, any type of structure can be applied provided that it is a sensor that can sense that the electronic cassette 20 has been loaded at a predetermined position of the accommodating portion 64, and that the electronic cassette 20 has been removed from the predetermined position of the accommodating portion 64.

In step 202, control is carried out such that a function that renders control by operation with respect to the operation unit 50 ineffective (a function that locks the operation unit 50) is selected. Due thereto, the operation unit 50 is locked by the cassette controller 120 such that input operation with respect to the operation unit 50 becomes impossible. For example, if the operation unit 50 is formed from dials or keys and switches, these are locked mechanically. If the operation unit 50 is structured by a touch panel, the touch panel is controlled to a state in which usage thereof is impossible. In step 202, an example is given of a case in which the operation unit 50 is locked such that input operation to the operation unit 50 is impossible. However, input operations received by the operation unit 50 may be rendered ineffective without locking the operation unit 50. Examples of this case are a form in which an input operation is received by the operation unit 50 and the signal corresponding to this input operation is not outputted to the cassette controller 120, and a form in which an input operation is received by the operation unit 50, the signal corresponding to this input operation is outputted to the cassette controller 120, and the signal is invalidated by the cassette controller 120. In this way, in present step 202, it suffices to carry out control such that the control by input operation with respect to the operation unit 50 is rendered ineffective.

In step 204, the routine stands-by until the electronic cassette 20 is removed from the predetermined position of the accommodating portion 64. Namely, the routine stands-by until the microswitches 76, 78 are turned off.

In step 206, the routine stands-by until a predetermined time period (here, 15 seconds) elapses from ending of the processing of step 204 (from the electronic cassette 20 being removed from the predetermined position of the accommodating portion 64). In step 208, control is carried out such that the function that renders control by operation with respect to the operation unit 50 effective (the function that releases the locking of the operation unit 50) is selected, and thereafter, the present electronic cassette control processing program ends. Due to the processing of step 208, the locked state of the operation unit 50 is cancelled by the cassette controller 120.

In the imaging system 10 relating to the present first exemplary embodiment, while the electronic cassette 20 is loaded at the predetermined position of the accommodating portion 64, i.e., while the operation unit 50 is locked, operation of the imaging device 36 (e.g., turning on/off of the power supply of the electronic cassette 20) is controlled by the console 26 carrying out wireless communication with the electronic cassette 20.

In the above-described electronic cassette control processing program, the routine stands-by until a predetermined time period elapses from the end of the processing of step 204. However, the present invention is not limited to the same, and the processing of above-described 208 may be carried out without carrying out the processing of above step 206 after the end of the processing of step 204. The above-described electronic cassette control processing program, and a program, in which the processing of step 206 is removed from the above-described electronic cassette control processing program, may be held in the cassette controller 120, and either program may be executed in accordance with the instruction of the user via the console 26.

As described above in detail, when a first condition expressing that the housing 34 is loaded at a predetermined position of the operating table 16 (here, the condition that the microswitches 76, 78 are on) is established, the electronic cassette 20 relating to the present first exemplary embodiment carries out control such that the function, that renders ineffective control by operation of the operation unit 50, is selected. When a second condition expressing that the housing 34 is not loaded at a predetermined position of the operating table 16 (here, the condition that the microswitches 76, 78 are off) is established, the electronic cassette 20 carries out control such that the function, that renders effective control by operation of the operation unit 50, is selected. When the operation unit 50 is operated, the function that has been controlled to be selected is executed. In this way, erroneous working due to erroneous operation when the electronic cassette 20 is loaded in the operating table 16 can be prevented.

In the electronic cassette 20 relating to the present first exemplary embodiment, the cassette controller 120 carries out control such that input operation with respect to the operation unit 50 is made to be impossible for an extended predetermined time period. Due thereto, erroneous working due to erroneous operation during a predetermined time period even after the electronic cassette 20 has been removed from the predetermined position of the operating table 16, can be prevented.

The imaging system 10 relating to the present first exemplary embodiment is structured to include the electronic cassette 20, and the console 26 that carries out communication, with the electronic cassette 20 loaded at a predetermined position of the operating table 16, for controlling operation of the imaging device 36. In this way, when the electronic cassette 20 is loaded in the operating table 16, operation of the imaging device 36 can be controlled by communication without utilizing the operation unit 50.

Second Exemplary Embodiment

A second exemplary embodiment of the present invention will be described. Other than the structure of a portion of the electronic cassette, the structure of the imaging system relating to the present second exemplary embodiment is the same as that of the imaging system 10 relating to the above-described first exemplary embodiment, and therefore, description thereof is omitted here. In the present second exemplary embodiment, only the portions that differ from the first exemplary embodiment will be described.

Figure 8:
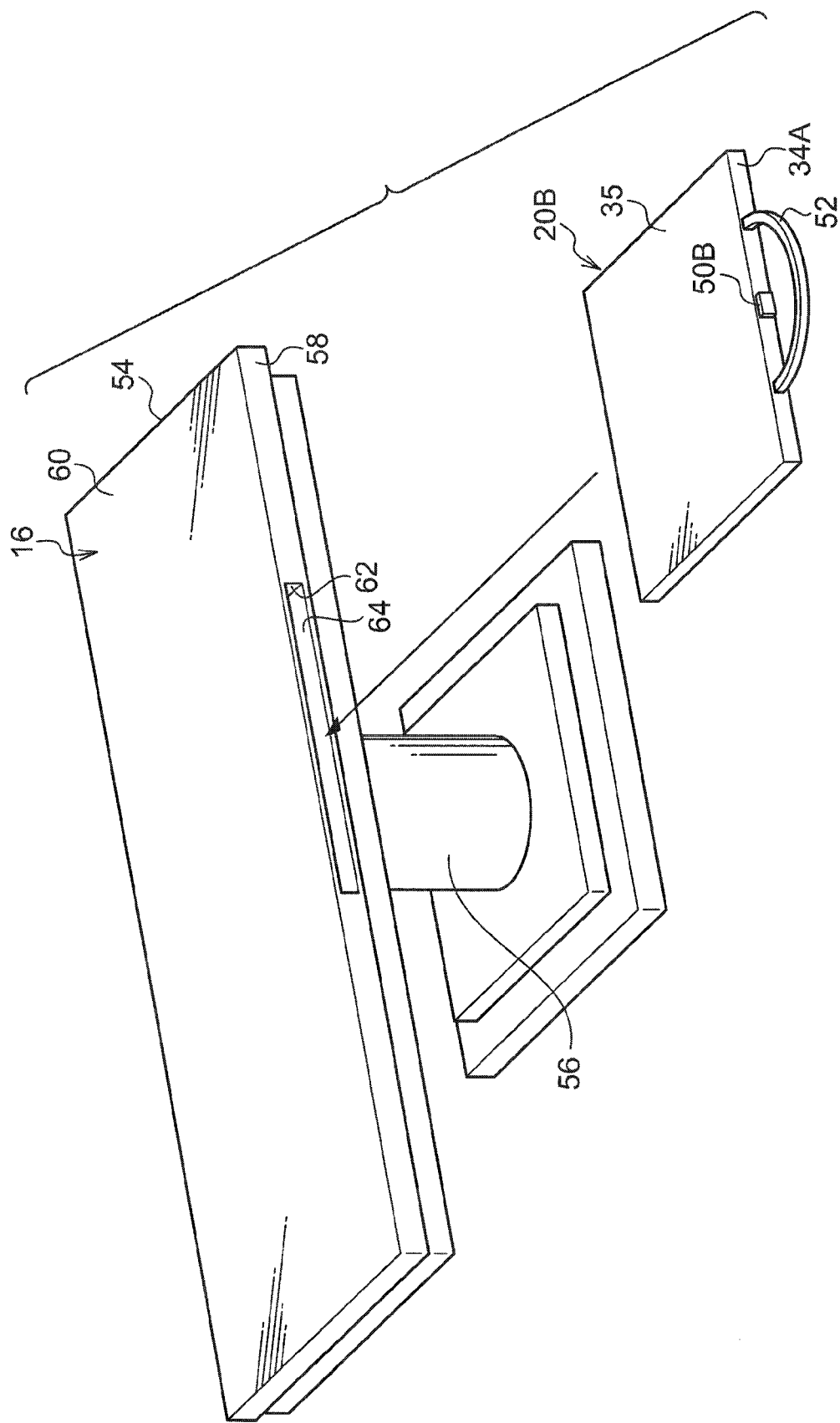
FIG. 8 is a perspective view showing the external appearance of an operating table and an electronic cassette relating to a second exemplary embodiment.

A perspective view showing the external appearance of the operating table 16 and an electronic cassette 20B relating to the present second exemplary embodiment is shown in FIG. 8.

As shown in FIG. 8, as compared with the electronic cassette 20 described in the first exemplary embodiment, the electronic cassette 20B differs with regard to the point that an operation unit 50B is provided instead of the operation unit 50. The operation unit 50B relating to the present second exemplary embodiment is structured by one push switch, and is operated when selecting the target function from among plural different functions relating to radiographic image capturing (in the present second exemplary embodiment, two functions that are a function of executing transmission to the console 26 of image information obtained by image capturing (hereinafter also called "first function"), and a function of turning the power supply on/off (hereinafter also called "second function")).

Figure 9:
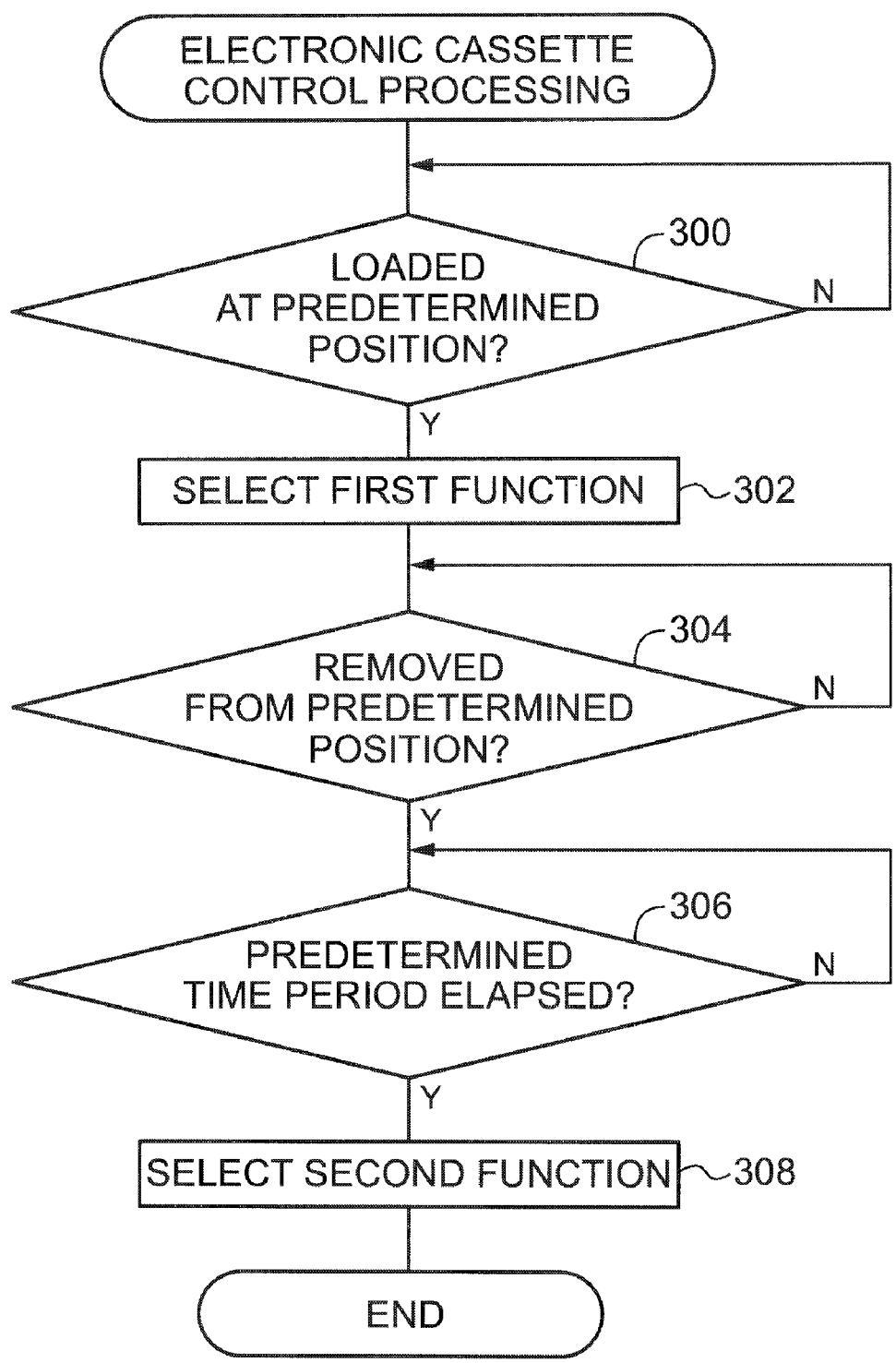
FIG. 9 is a flowchart showing the flow of processings of an electronic cassette control processing program relating to the second exemplary embodiment.

A processing routine of the electronic cassette 20B at the time when the power supply of the electronic cassette 20B is turned on will be described with reference to FIG. 9. FIG. 9 is a flowchart showing the flow of processings of an electronic cassette control processing program that is executed by the cassette controller 120 of the electronic cassette 20B at this time. This program is stored in advance in a predetermined region of a memory that is contained in the microcomputer that realizes the cassette controller 120.

In step 300 of FIG. 9, the routine stands-by until the electronic cassette 20B is loaded at a predetermined position of the accommodating portion 64. In step 302, control is carried out such that the first function is selected. Due thereto, the operation unit 50B functions as a transmission executing switch for starting transmission to the console 26 of the image information obtained by image capturing. When the operation unit 50B is operated, the transmission of image information to the console 26 is implemented by the cassette controller 120.

In step 304, the routine stands-by until the electronic cassette 20B is removed from the predetermined position of the accommodating portion 64. In step 306, the routine stands-by until a predetermined time period (here, 15 seconds) elapses from the end of the processing of step 304 (from the electronic cassette 20B being removed from the predetermined position of the accommodating portion 64).

In step 308, control is carried out such that the second function is selected, and thereafter, the present electronic cassette control processing program ends. Due to the processing of step 308, the operation unit 50B functions as a power switch for turning the power supply on/off, and, when the operation unit 50B is operated, switching of the on/off state of the power supply is executed by the cassette controller 120.

In the present second exemplary embodiment, while the electronic cassette 20B is loaded at the predetermined position of the accommodating portion 64, i.e., while the operation unit 50B is functioning as a transmission executing switch, operation of the imaging device 36 (e.g., turning on/off of the power supply of the electronic cassette 20B) is controlled by the console 26 carrying out wireless communication with the electronic cassette 20B.

As described above in detail, when a first condition expressing that the housing 34 is loaded at a predetermined position of the operating table 16 (here, the condition that the microswitches 76, 78 are on) is established, the electronic cassette 20B relating to the present second exemplary embodiment carries out control such that the function that should be rendered effective when the first condition is established (here, the function of executing transmission to the console 26 of the image information obtained by image capturing) is selected. When a second condition expressing that the housing 34 is not loaded at the predetermined position of the operating table 16 (here, the condition that the microswitches 76, 78 are off) is established, the electronic cassette 20B carries out control such that the function that should be rendered effective when the second condition is established (here, the function of turning the power supply on/off) is selected. When the operation unit 50B is operated, the function that is controlled so as to be selected is implemented. Due thereto, erroneous working due to erroneous operation when the electronic cassette 20B is loaded in the operating table 16 can be prevented.

The present invention has been described here by using the above respective exemplary embodiments, but the technical scope of the present invention is not limited to the scopes recited in the above exemplary embodiments.

For example, the above first exemplary embodiment describes an example of a case in which, when the electronic cassette 20 is loaded at the predetermined position of the accommodating portion 64 of the operating table 16, the operation unit 50 is locked so that inputting operation with respect to the operation unit 50 becomes impossible. However, the present invention is not limited to the same. For example, the operation unit 50 may be locked such that inputting operation with respect to the operation unit 50 becomes impossible, when the electronic cassette 20 is placed at a predetermined position of the top surface 60 of the placement stand 54 of the operating table 16.

The above second exemplary embodiment describes the example of a case in which the function of executing transmission to the console 26 of the image information obtained by image capturing is used as the first function, and the function of turning the power supply on/off is used as the second function. However, the present invention is not limited to the same. Any functions can be used as the first and second functions provided that a function, that does not impede image capturing even if executed due to the operation unit 50B being operated when the housing 34 is loaded at a predetermined position of the operating table 16, is used as the first function, and a function, that does not impede image capturing even if executed due to the operation unit 50B being operated when the housing 34 is not loaded at the predetermined position of the operating table 16, is used as the second function.

Although the above second exemplary embodiment describes an example of a case in which the operation unit 50B is structured by a single push switch, the present invention is not limited to the same. The operation unit 50B may be structured by plural switches as is the operation unit 50 described in the first exemplary embodiment. In this case, it suffices to change only the function of at least one switch among the plural switches when the first condition or the second condition is established.

Although the above respective exemplary embodiment describe examples of cases in which the electronic cassette 20, 20B is loaded in the accommodating portion 64 of the operating table 16, the present invention is not limited to the same. The present invention can also be applied to cases in which the electronic cassette 20, 20B is placed in a cradle for carrying out charging of the electronic cassette 20, 20B, or is placed at a predetermined placement portion of a storage box for storing the electronic cassette 20, 20B. The judgment as to whether or not the electronic cassette 20, 20B is placed in the cradle may be carried out by judging, for example, whether or not communication with the console 26 has been established, or whether or not charging has started.

Further, the above respective exemplary embodiments describe examples of cases in which the operating table 16 that is used in an operating room is used as the imaging stand, but the present invention is not limited to the same. For example, the imaging stand may be an imaging stand that is used in a room that is specially used for capturing of radiographic images, or may be an imaging stand that is used at the time of capturing radiographic images.

Third Exemplary Embodiment

Figure 10:
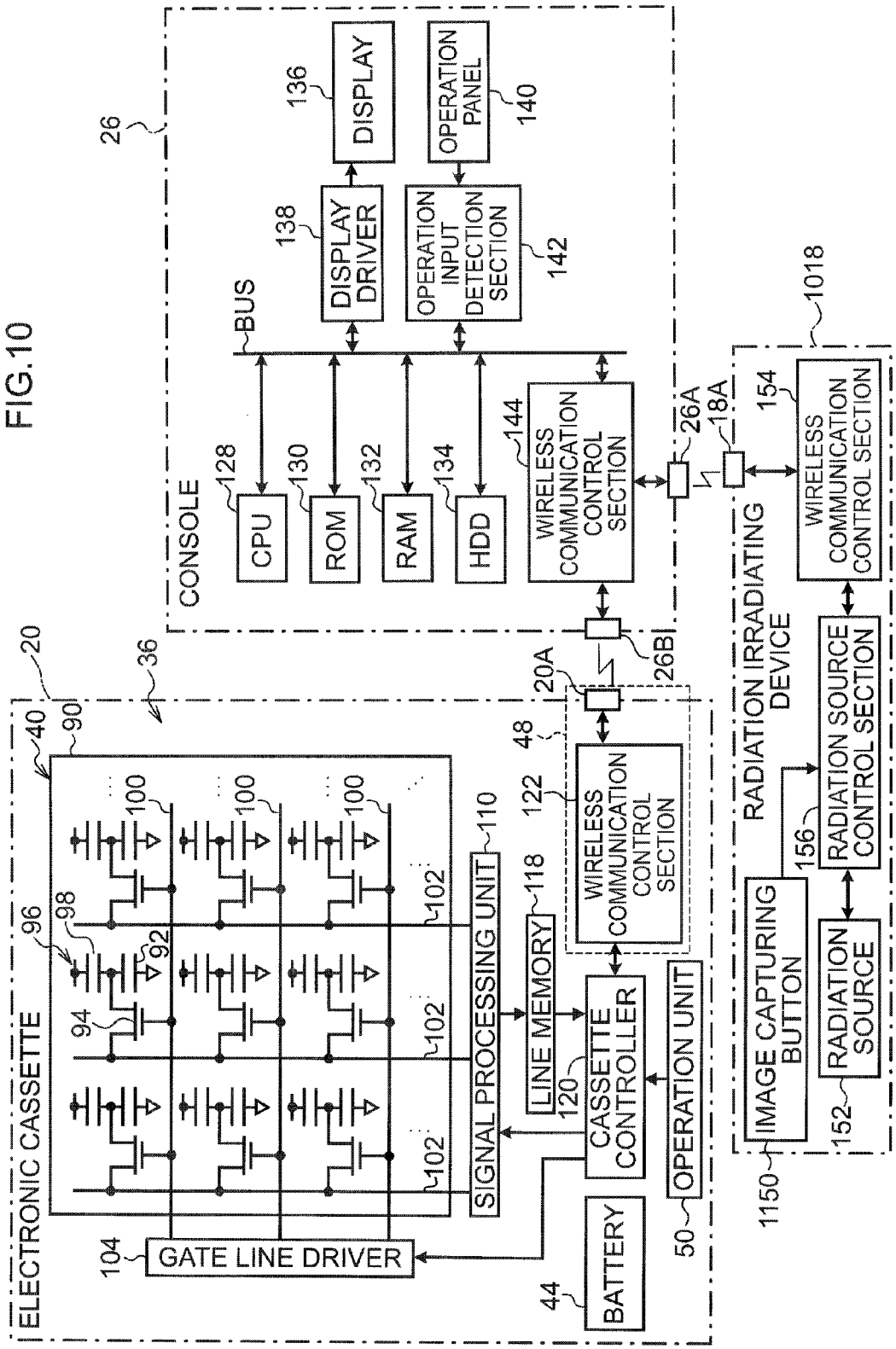
FIG. 10 is a block diagram showing the structure of main portions of an imaging system relating to a third exemplary embodiment.

A block diagram showing structures of main portions of the imaging system 10 relating to the present exemplary embodiment is shown in FIG. 10.

A radiation irradiating device 1018 has an image capturing button 1150 that is pushed and operated by a user when he/she implements image capturing. Because the other structures are the same as those of FIG. 5, description thereof is omitted.

The image capturing button 1150 relating to the present exemplary embodiment is structured such that pushing operations of two stages, that are a state of being depressed to an intermediate position (hereinafter called "half depressed state") and a state of being pushed to a final pushed position that is past the intermediate position (hereinafter called "fully depressed state"), can be detected.

At the radiation irradiating device 1018 relating to the present exemplary embodiment, when the image capturing button 1150 is set in the half depressed state by a user, the image capturing button 1150 outputs, to the radiation source controller 156, an accumulation instruction signal (irradiation preparation signal) that instructs that energy for irradiating the radiation X be accumulated at the radiation source 152, and transmits the accumulation instruction signal to the console 26 via the wireless communication controller 154 and the antenna 18A. When the accumulation instruction signal is inputted thereto, the radiation controller 156 carries out control so as to accumulate that energy at the radiation source 152. When the CPU 128 of the console 26 receives the accumulation instruction signal, the CPU 128 transmits the accumulation instruction signal to the electronic cassette 20 via the wireless communication controller 144 and the antenna 26B. By receiving the accumulation instruction signal, the cassette controller 120 of the electronic cassette 20 considers that preparations for irradiating the radiation X at the radiation irradiating device 1018 have been completed.

If the user continues to depress the image capturing button 1150 to the fully depressed state, the image capturing button 1150 outputs, to the radiation controller 156, an irradiation instruction signal that instructs irradiation of the radiation X. In accordance therewith, the radiation controller 156 carries out control such that radiation is irradiated from the radiation source 152 by using the energy accumulated in the radiation source 152.

Figure 11:
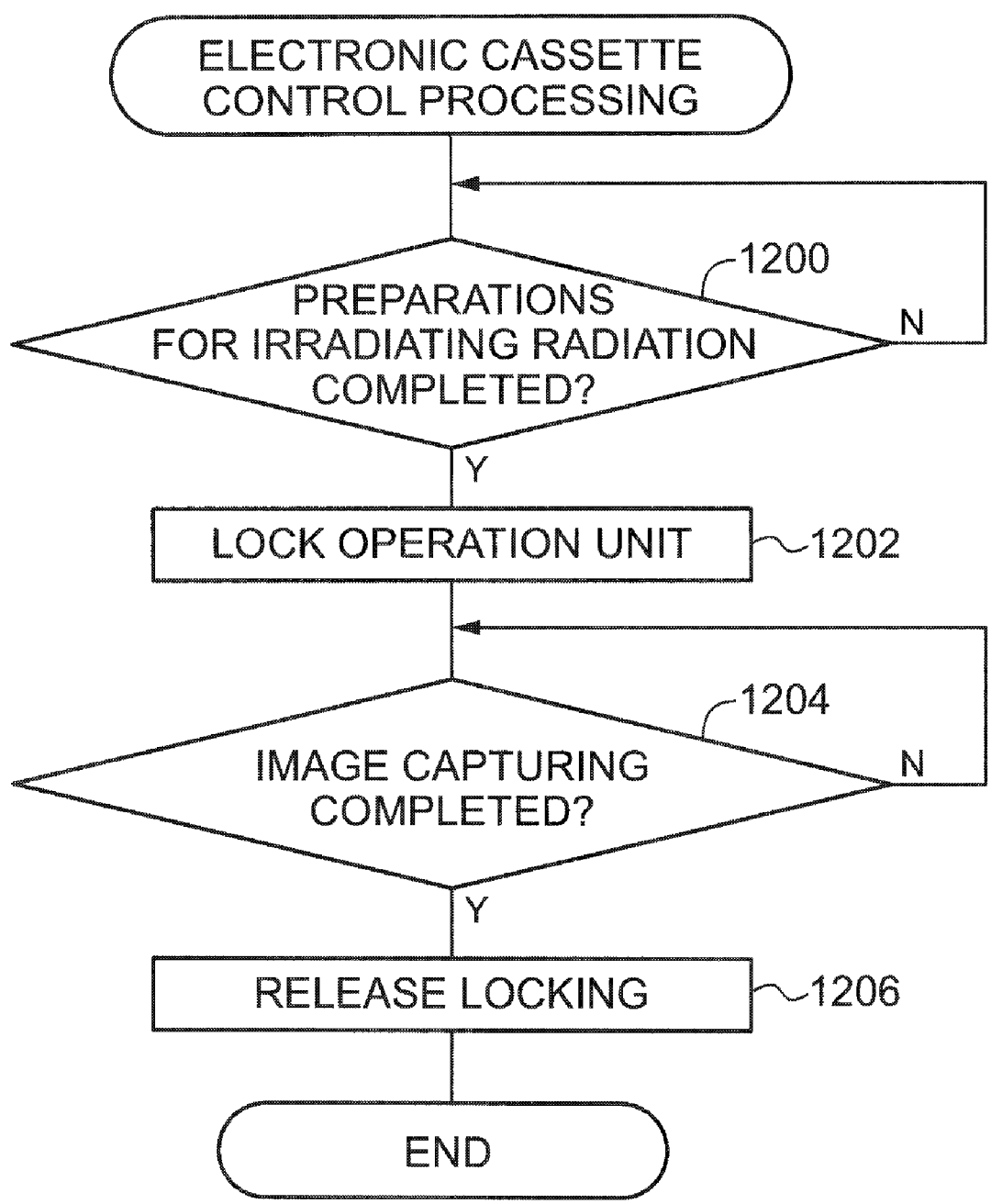
FIG. 11 is a flowchart showing the flow of processings of an electronic cassette control processing program relating to the third exemplary embodiment.

A processing routine of the electronic cassette 20 when the power supply of the electronic cassette 20 is turned on will be described with reference to FIG. 11. FIG. 11 is a flowchart showing the processings of an electronic cassette control processing program that is executed by the cassette controller 120 of the electronic cassette 20 at this time. This program is stored in advance in a predetermined region of a memory included in the microcomputer that realizes the cassette controller 120.

In step 1200 of FIG. 11, completion of the preparations for irradiating the radiation X at the radiation irradiating device 1018 is awaited. Namely, in present step 1200, reception of the accumulation instruction signal transferred from the console 26 is awaited, and, due to this accumulation instruction signal being received, it is judged that preparations for irradiating the radiation X have been completed. In the present electronic cassette control processing program, the processing of awaiting completion of the preparations for irradiating the radiation X at the radiation irradiating device 1018 is used as the processing of step 1200, but the present invention is not limited to the same. For example, the processing of awaiting the setting of the electronic cassette 20 at the operating table 16, the processing of awaiting turning on of the power supply of the radiation irradiating device 1018, or the like may be used. Any type of processing may be used provided that it is a processing that awaits completion of a processing by which preparations for carrying out image capturing are possible.

In step 1202, control is carried out such that the function that renders control by operation of the operation unit 50 (see FIG. 2) ineffective (the function of locking the operation unit 50) is selected. Due thereto, the operation unit 50 is locked by the cassette controller 120 such that input operation with respect to the operation unit 50 becomes impossible. For example, if the operation unit 50 is formed from dials or keys and switches, these are locked mechanically. If the operation unit 50 is structured by a touch panel, the touch panel is controlled to a state in which usage thereof is impossible. In step 1202, an example is shown of a case in which the operation unit 50 is locked such that input operation to the operation unit 50 is impossible. However, the input operation received by the operation unit 50 may be rendered ineffective without locking the operation unit 50. Examples of this case are a form in which an input operation is received by the operation unit 50 and the signal corresponding to this input operation is not outputted to the cassette controller 120, and a form in which an input operation is received by the operation unit 50, the signal corresponding to this input operation is outputted to the cassette controller 120, and the signal is invalidated by the cassette controller 120. In this way, in present step 1202, it suffices to carry out control such that control by the input operation with respect to the operation unit 50 is rendered ineffective.

In step 1204, awaiting the completion of image capturing is carried out. At the electronic cassette 20 relating to the present third exemplary embodiment, image capturing is considered completed on account of the image information outputted from the signal processing unit 110 being stored via the line memory 118 in a predetermined storage region of the cassette controller 120 (here, a memory included in the microcomputer). However, the present invention is not limited to the same. For example, image capturing may be considered as completed on account of a predetermined time period (e.g., a time period determined in advance as the time period over which image information is stored in the predetermined storage region) having elapsed from the releasing of the fully depressed state of the image capturing button 1150. Image capturing may be considered to be completed on account of the image information of a number of shots specified by the user (e.g., four shots) being stored in the predetermined storage region of the cassette controller 120 via the line memory 118.

In step 1206, control is carried out such that the function that renders control by operation with respect to the operation unit 50 effective (the function of releasing the locking of the operation unit 50) is selected, and thereafter, the present electronic cassette control processing program ends. Due to the processing of step 1206, the locked state of the operation unit 50 is cancelled by the cassette controller 120.

In the imaging system 10 relating to the present exemplary embodiment, while the operation unit 50 is locked, operation of the imaging device 36 (e.g., the turning on/off of the power supply of the electronic cassette 20) is controlled by the console 26 carrying out wireless communication with the electronic cassette 20.

As described above in detail, at the electronic cassette 20 relating to the present third exemplary embodiment, during a predetermined time period (the time period from the completion of preparations for irradiating the radiation X at the radiation radiating device 1018 until the completion of image capturing), control is carried out such that the function that renders ineffective control by operation with respect to the operation unit 50 is selected. The function that has been controlled to be selected is executed when the operation unit 50 is operated. In this way, erroneous working due to erroneous operation during a predetermined time period can be prevented.

Fourth Exemplary Embodiment

The fourth exemplary embodiment uses the electronic cassette 20B at which the operation unit 50B is provided instead of the operation unit 50, as compared with the electronic cassette 20 described in the first exemplary embodiment. The operation unit 50B is structured by a single push switch, and is operated at the time of selecting the target function from among plural different functions relating to radiographic image capturing (in the present fourth exemplary embodiment, two functions that are a function that executes transmission to the console 26 of the image information obtained by image capturing (hereinafter also called "first function") and a function that turns the power supply on/off (hereinafter also called "second function").

Figure 12:
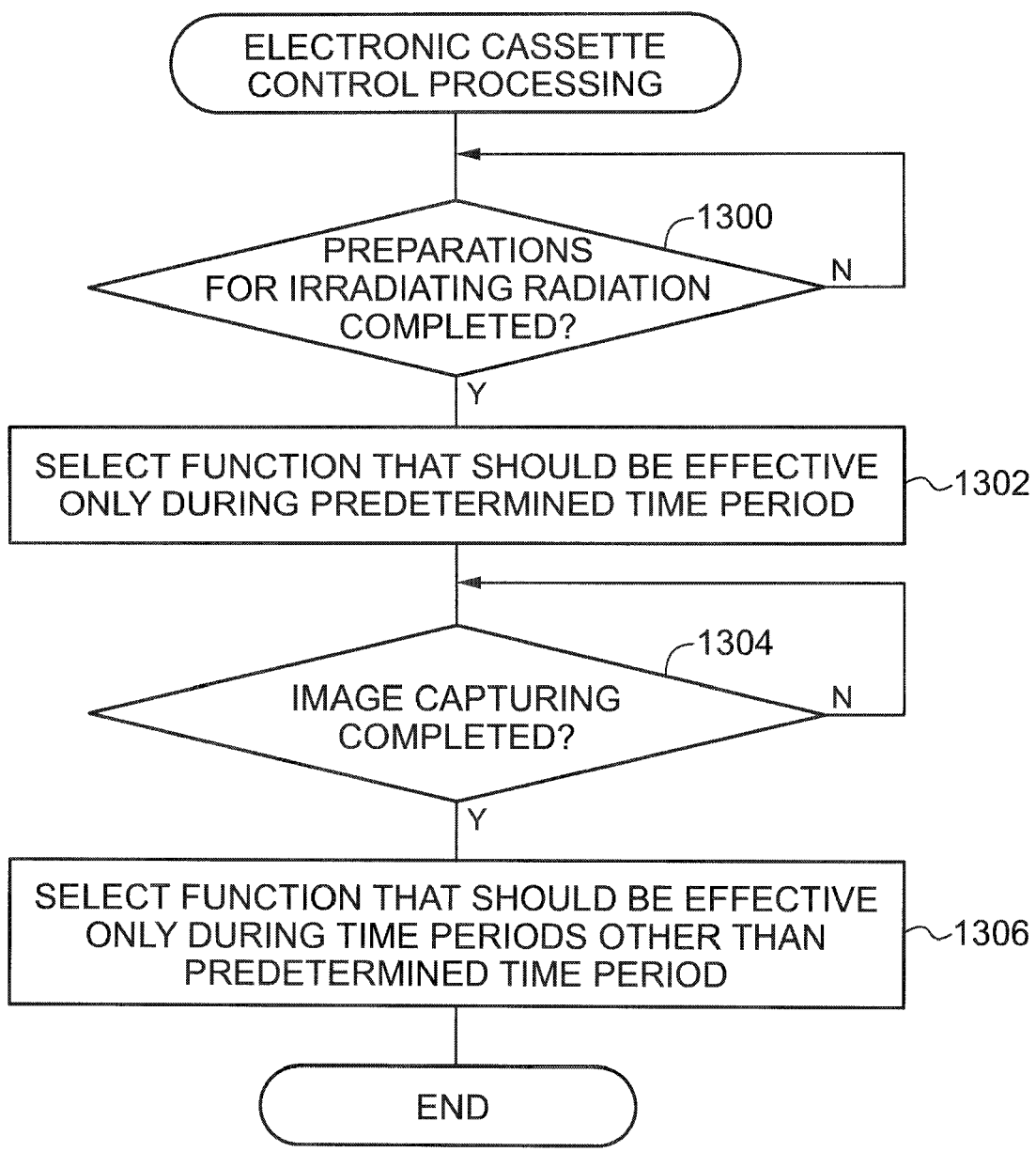
FIG. 12 is a flowchart showing the flow of processings of an electronic cassette control processing program relating to a fourth exemplary embodiment.

FIG. 12 is a flowchart showing the flow of processings of an electronic cassette control processing program executed by the cassette controller 120 of an electronic cassette 20B when an accumulation instruction signal transferred from the console 26 is received. This program is stored in advance in a predetermined region of a memory that is included in the microcomputer that realizes the cassette controller 120.

In step 1300 of FIG. 12, completion of the preparations for irradiating the radiation X at the radiation irradiating device 18 is awaited. In step 1302, control is carried out such that the first function is selected as the function that is to be effective only during the time period from the completion of preparations for irradiating the radiation X at the radiation radiating device 18 until completion of the image capturing. Due thereto, the operation unit 50B functions as a transmission executing switch for executing transmission to the console 26 of the image information obtained by image capturing. When the operation unit 50B is operated, transmission of image information to the console 26 is executed by the cassette controller 120.

In step 1304, awaiting completion of image capturing is carried out. At the electronic cassette 20B relating to the present fourth exemplary embodiment, image capturing is considered to be completed on account of the image information outputted from the signal processing unit 110 being stored via the line memory 118 in a predetermined storage region of the cassette controller 120 (here, a memory included in the microcomputer). However, the present invention is not limited to the same. For example, image capturing may be considered as completed on account of a predetermined time period (e.g., a time period determined in advance as the time period over which image information is stored in the predetermined storage region) having elapsed from the releasing of the fully depressed state of the image capturing button 1150 of the radiation irradiating device 1018.

In step 1306, control is carried out such that the second function is selected as the function that is to be effective only during time periods other than the time period from completion of preparations for irradiating the radiation X at the radiation irradiating device 18 until image capturing is completed. Thereafter, the present electronic cassette control processing program ends. Due to the processing of step 1306, the operation unit 50B functions as a power switch for turning the power supply on/off, and, when the operation unit 50B is operated, switching of the on/off of the power supply is executed by the cassette controller 120.

In the present fourth exemplary embodiment, the electronic cassette 20B is controlled such that the power supply of the electronic cassette 20B is turned on/off by the console 26 carrying out wireless communication with the electronic cassette 20B during the time period from completion of the preparations for irradiating the radiation X at the radiation irradiating device 18 until completion of image capturing, i.e., during the time period when the operation unit 50B functions as a transmission starting switch.

As described above in detail, at the electronic cassette 20B relating to the present fourth exemplary embodiment, during a predetermined time period (the time period from the completion of preparations for irradiating the radiation X at the radiation radiating device 18 to the completion of image capturing), control is carried out such that the function that should be effective only during that predetermined time period is selected. The function that has been controlled to be selected is executed when the operation unit 50B is operated. In this way, erroneous working due to erroneous operation during a predetermined time period can be prevented.

Fifth Exemplary Embodiment

Figure 13:
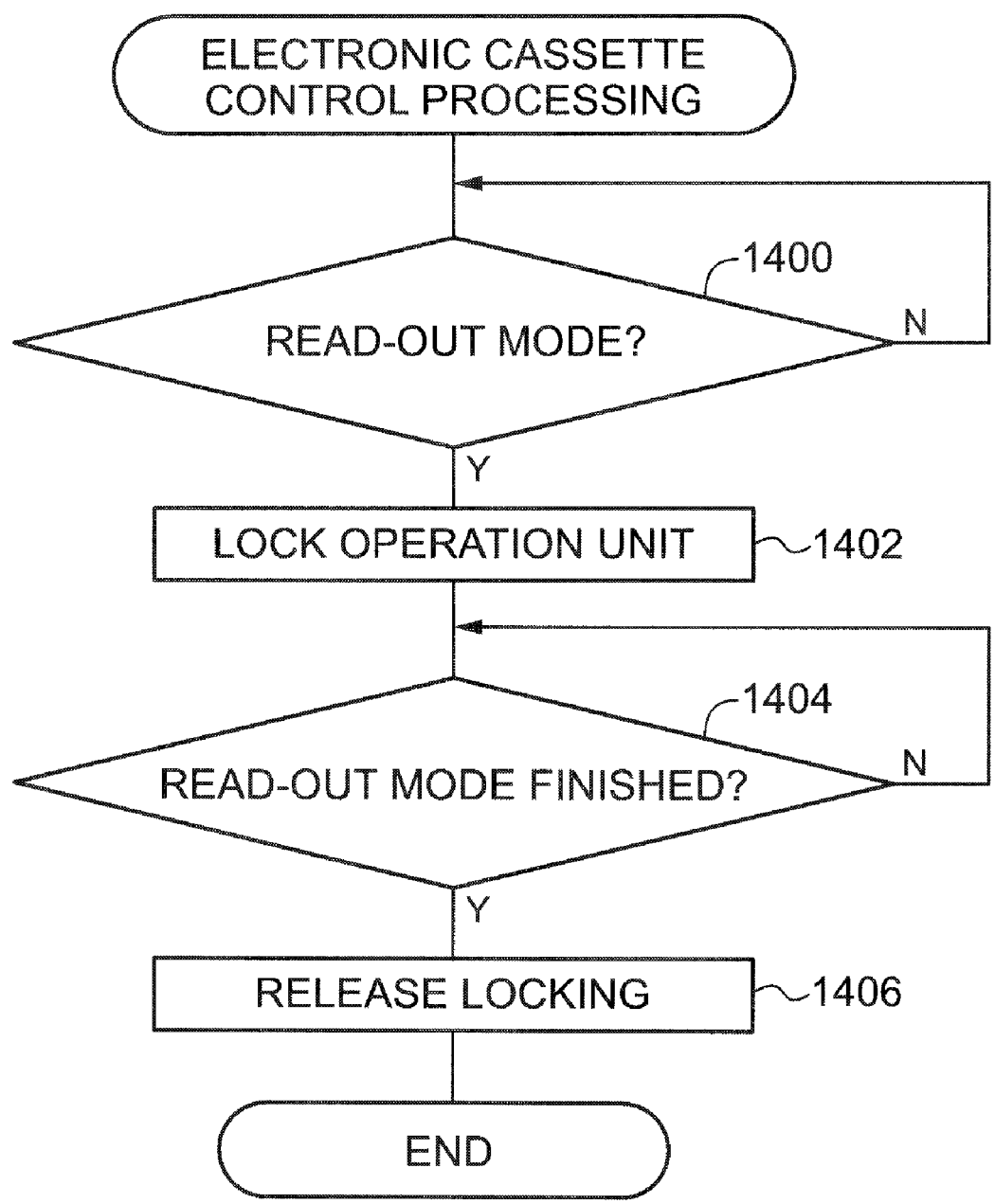
FIG. 13 is a flowchart showing the flow of processings of an electronic cassette control processing program relating to a fifth exemplary embodiment.

FIG. 13 is a flowchart showing the flow of processings of an electronic cassette control processing program executed by the cassette controller 120 of the electronic cassette 20 (see FIG. 2) when an accumulation instruction signal transferred from the console 26 is received. This program is stored in advance in a predetermined region of a memory that is included in the microcomputer that realizes the cassette controller 120.

In step 1400 of FIG. 13, the routine stands-by until the mode becomes a read-out mode that reads-out image information via the line memory 118 from the signal processing unit 110 in order to store the image information in a predetermined storage region (here, a memory included in the microcomputer of the cassette controller 120). In step 1402, control is carried out such that a function, that renders the control by operation of the operation unit 50 ineffective (the function of locking the operation unit 50), is selected. Due thereto, the operation unit 50 is locked by the cassette controller 120 such that input operation with respect to the operation unit 50 becomes impossible.

In step 1404, the end of the read-out mode is awaited. In step 1406, control is carried out such that a function, that renders the control by operation of the operation unit 50 effective (the function of releasing the locking of the operation unit 50), is selected, and thereafter, the present electronic cassette control processing program ends. Due to the processing of step 1406, the locked state of the operation unit 50 is cancelled by the cassette controller 120.

As described above in detail, at the electronic cassette 20 relating to the present fifth exemplary embodiment, control is carried out such that the function that renders ineffective control by operation with respect to the operation unit 50 is selected, during the time period (the time of the read-out mode) from the start of output of electric signals (here, image information) by the radiation detector 40 to a predetermined storage region (here, a memory included in the microcomputer of the cassette controller 120), until the completion of radiographic image capturing. Control is carried out such that the function that renders effective control by operation with respect to the operation unit 50 is selected during the time period (at times other than the read-out mode) from completion of preparations for irradiating the radiation for radiographic image capturing until the radiographic image capturing is completed. The function that is controlled so as to be selected is executed when the operation unit 50 is operated. Due thereto, erroneous working due to erroneous operation at the time of the read-out mode can be prevented.

An example has been described of a case in which, in the electronic cassette 20 relating to the present fifth exemplary embodiment, the operation unit 50 is locked during the read-out mode, but the present invention is not limited to the same. For example, in addition to the time of the read-out mode, the operation unit 50 may be locked also at the time of a transmission mode in which the electronic cassette 20 transmits the image information to the console 26, or the operation unit 50 may be locked only at the time of the transmission mode. In this case, image capturing is considered to be completed on account of the image information being stored in a predetermined storage region (e.g., the HDD 134) of the console 26.

The operation unit 50 may be locked during the time period from the start of conversion of the radiation X into electric signals by the radiation detector 40 until the completion of image capturing. In this case, image capturing is considered to be completed on account of the electric signals (image information) being stored in a predetermined storage region (e.g., a memory included in the microcomputer of the cassette controller 120).

By locking the operation unit 50 during a predetermined time period in this way, erroneous working due to erroneous operation during that predetermined time period can be prevented.

The present fifth exemplary embodiment describes an example of a case in which the operation unit 50 is locked at the time of the read-out mode, and the locked state of the operation unit 50 is cancelled at times other than the time of the read-out mode. However, the present invention is not limited to the same. Control may be carried out such that, at the time of the read-out mode, the function that should be effective only at the time of the read-out mode (as an example, the first function described in the above fourth exemplary embodiment) is selected. At times other than the time of the read-out mode, control may be carried out such that the function that should be effective only at times other than the time of the read-out mode (as an example, the second function described in the above fourth exemplary embodiment) is selected. In this way, the function that is controlled so as to be selected may be executed at the time when the operation unit 50 is operated.

Control may be carried out such that, during the time period from the start of conversion of the radiation X into electric signals by the radiation detector 40 until the completion of image capturing, the function, that should be effective only during the time period from the start of conversion of the radiation X into electric signals by the radiation detector 40 until the completion of image capturing, is selected. During time periods other than the time period from the start of conversion of the radiation X into electric signals by the radiation detector 40 until the completion of image capturing, control may be carried out such that the function, that should be effective only during the time periods other than the time period from the start of conversion of the radiation X into electric signals by the radiation detector 40 until the completion of image capturing, is selected. The function that is controlled so as to be selected may be executed when the operation unit 50 is operated. In this case, for example, during the time period from the start of conversion of the radiation X into electric signals by the radiation detector 40 until the completion of image capturing, it is possible to prevent noise, that is generated by fluctuations in the power supply that accompany changing of the mode due to the operation unit 50 being operated erroneously, from being superposed on the electric signals.

The present invention has been described above by using the respective exemplary embodiments, but the technical scope of the present invention is not limited to the scopes described in the above respective exemplary embodiments.

For example, the third exemplary embodiment describes an example of a case in which the image capturing button 1150 is included at the radiation irradiating device 1018, but the present invention is not limited to the same. The image capturing button 1150 may be provided at the console 26. An instruction to prepare for irradiation of the radiation X and an instruction to irradiate the radiation X may be given to the radiation irradiating device 1018 via the operation panel 140 of the console 26, without providing the image capturing button 1150. The instruction to prepare for irradiation of the radiation X may be given to the radiation irradiating device 1018 via the operation panel 140 of the console 26, and the instruction to irradiate the radiation X may be given by the image capturing button 1150. The instruction to prepare for irradiation of the radiation X may be given to the radiation irradiating device 1018 by the image capturing button 1150, and the instruction to irradiate the radiation X may be given via the operation panel 140 of the console 26.

In the above fourth exemplary embodiment, an example is described of a case in which the function that executes transmission to the console 26 of the image information obtained by image capturing is used as the first function, and the function that turns the power supply on/off is used as the second function. However, the present invention is not limited to the same. Any functions may be used as the first and second functions provided that a function, that does not impede image capturing even if executed due to the operation unit 50B being operated during the time period from completion of preparations for irradiating the radiation X at the radiation irradiating device 18 until completion of the image capturing, is made to be the first function, and a function, that does not impede image capturing even if executed due to the operation unit 50B being operated during time periods other than the time period from completion of preparations for irradiating the radiation X at the radiation irradiating device 18 until completion of the image capturing, is made to be the second function.

The above fourth exemplary embodiment describes an example of a case in which the function of the operation unit 50B is changed between the time period, that is from completion of preparations for irradiating the radiation X at the radiation irradiating device 18 until completion of the image capturing, and time periods other than that. However, the present invention is not limited to the same. If there are plural image capturing steps during the time period from the start of capturing of a radiographic image to the end of capturing, the function of the operation unit 50B may be changed dynamically by the cassette controller 120 at each image capturing step. Due thereto, appropriate functions can be assigned to the operation unit 50B at each of the image capturing steps, and erroneous working due to erroneous operation at each image capturing step can be prevented. The optimal function can be selected on each occasion, and the erroneous selection of a function that is not needed can be prevented.

In addition, the structures of the imaging system 10 (see FIG. 1, FIG. 3, FIG. 4, FIG. 5 and FIG. 10), and the structures of the electronic cassettes 20, 20B (see FIG. 2, FIG. 5, FIG. 6 and FIG. 8) that are described in the above respective exemplary embodiments are examples, and changes can, of course, be made thereto in accordance with the situation within a scope that does not deviate from the gist of the present invention.

Further, the flows of the processings of the programs described in the above respective exemplary embodiments (refer to FIG. 7, FIG. 9, FIG. 11, FIG. 13 and FIG. 14) also are examples. Unnecessary steps thereof may be deleted, new steps may be added thereto, or the order of the processings thereof may be rearranged within a scope that does not deviate from the gist of the present invention.

Although the present invention has been described above by using the respective exemplary embodiments, the technical scope of the present invention is not limited to the scopes described in the above exemplary embodiments.

In accordance with a first aspect of the present invention, there is provided a portable radiographic imaging device including: an operation unit operated when selecting a target function from a plurality of different functions relating to radiographic image capturing; a controller that, when a first condition, that expresses that a predetermined region has been placed at a predetermined placement portion, is established, carries out control such that a function that should be effective when the first condition is established is selected, and, when a second condition, that expresses that the predetermined region is not placed at the placement portion, is established, carries out control such that a function that should be effective when the second condition is established is selected; and an execution unit that, when the operation unit is operated, executes a function that is controlled by the controller to be selected.

In accordance with the portable radiographic imaging device relating to the first aspect, when the first condition, that expresses that the predetermined region has been placed at the predetermined placement portion, is established, control is carried out such that the function that should be effective when the first condition is established is selected. When the second condition, that expresses that the predetermined region is not placed at the predetermined placement portion, is established, control is carried out such that the function that should be effective when the second condition is established is selected. The function, that is controlled to be selected, is executed when the operation unit is operated. Due thereto, a erroneous working due to erroneous operation when the predetermined region is placed at the predetermined placement portion can be prevented.

In accordance with a second aspect of the present invention, there is provided a portable radiographic imaging device including: an operation unit operated when selecting a target function from a plurality of different functions relating to radiographic image capturing; a controller that, when a first condition, that expresses that a predetermined region has been placed at a predetermined placement portion, is established, carries out control such that a function that renders control by operation with respect to the operation unit ineffective is selected, and, when a second condition, that expresses that the predetermined region is not placed at the placement portion, is established, carries out control such that a function that renders control by operation with respect to the operation unit effective is selected; and an execution unit that, when the operation unit is operated, executes a function that is controlled by the controller to be selected.

In accordance with the portable radiographic imaging device relating to the second aspect, when the first condition, that expresses that the predetermined region has been placed at the predetermined placement portion, is established, control is carried out such that the function, that renders control by operation with respect to the operation unit ineffective, is selected. When the second condition, that expresses that the predetermined region is not placed at the predetermined placement portion, is established, control is carried out such that the function, that renders control by operation with respect to the operation unit effective, is selected. The function, that is controlled to be selected, is executed when the operation unit is operated. Due thereto, erroneous working due to erroneous operation when the predetermined region is placed at the predetermined placement portion can be prevented.

In accordance with a third aspect of the present invention, there is provided a radiographic imaging system including: a portable radiographic imaging device that includes: an operation unit operated when selecting a target function from a plurality of different functions relating to radiographic image capturing, a controller that, when a first condition, that expresses that a predetermined region has been placed at a predetermined placement portion, is established, carries out control such that a function that should be effective when the first condition is established is selected, and, when a second condition, that expresses that the predetermined region is not placed at the placement portion, is established, carries out control such that a function that should be effective when the second condition is established is selected, and an execution unit that, when the operation unit is operated, executes a function that is controlled by the controller to be selected; and a communication device that, when the first condition is established, causes the execution unit to execute the function that should be effective when the second condition is established, by carrying out communication with the portable radiographic imaging device.

Because the radiographic imaging system relating to the third aspect operates similarly to the portable radiographic imaging device relating to the first aspect, effects that are similar to those of the portable radiographic imaging device can be obtained. Further, when the first condition, that expresses that the predetermined region of the portable radiographic imaging device is placed at the predetermined placement portion, is established, the second function can be executed by communication without using the operation unit.

In accordance with a fourth aspect of the present invention, there is provided a radiographic imaging system including: a portable radiographic imaging device that comprises: an operation unit operated when selecting a target function from a plurality of different functions relating to radiographic image capturing, a controller that, when a first condition, that expresses that a predetermined region has been placed at a predetermined placement portion, is established, carries out control such that a function that renders control by operation with respect to the operation unit ineffective is selected, and, when a second condition, that expresses that the predetermined region is not placed at the placement portion, is established, carries out control such that a function that renders control by operation with respect to the operation unit effective is selected, and an execution unit that, when the operation unit is operated, executes a function that is controlled by the controller to be selected; and a communication device that, when the first condition is established, causes the execution unit to execute the function that renders control by operation with respect to the operation unit effective, by carrying out communication with the portable radiographic imaging device.

Because the radiographic imaging system relating to the fourth aspect operates similarly to the portable radiographic imaging device relating to the second aspect, effects that are similar to those of the portable radiographic imaging device can be obtained. Further, when the first condition, that expresses that the predetermined region of the portable radiographic imaging device is placed at the predetermined placement portion, is established, the function that renders control by operation with respect to the operation unit effective can be implemented by communication.

In accordance with the present invention, there is the effect that erroneous working due to erroneous operation when a predetermined region is placed at a predetermined placement portion can be prevented.

Although the present invention has been described above by using the respective exemplary embodiments, the technical scope of the present invention is not limited to the scopes recited in the exemplary embodiments. Various modifications or improvements can be made to the above respective exemplary embodiments within a scope that does not deviate from the gist of the present invention, and forms to which such modifications or improvements have been made also are included within the technical scope of the present invention.

Further, the above respective exemplary embodiments do not limit the invention recited in the claims, and it is not necessarily the case that all of the combinations of features described in the respective exemplary embodiments are essential to the means of the present invention for solving the problems of the conventional art. Inventions of various stages are included in the above exemplary embodiments, and various inventions can be extracted by combining, in accordance with the situation, plural structural features that are disclosed. Even if some of the structural features are removed from all of the structural features that are illustrated in the above respective exemplary embodiments, such structures from which some structural features are removed can be extracted as inventions provided that the effects of the present invention are obtained thereby.

What is claimed is:

1. A portable radiographic imaging device comprising:
an electronic imaging cassette having:
   an operation unit peripheral to an irradiating surface of the electronic imaging cassette, wherein the operation unit is configured to be operated when selecting a target function from a plurality of different functions relating to radiographic image capturing;
   a controller that, when a first condition is established, in which a predetermined region of the electronic imaging cassette has been placed at a predetermined position, causes a function associated with the first condition to be selectable via the operation unit, and, when a second condition is established, in which the predetermined region is not placed at the predetermined position, causes a function associated with the second condition to be selectable via the operation unit; and
   an execution unit that, when the operation unit is operated, executes a function that the controller causes to be selectable via the operating unit.

2. The portable radiographic imaging device of claim 1, wherein the function associated with the first condition is a function that transmits captured image information, and the function associated with the second condition is a function that turns a power supply on/off.

3. A portable radiographic imaging device comprising:
an electronic imaging cassette having:
   an operation unit peripheral to an irradiating surface of the electronic imaging cassette, wherein the operation unit is configured to be operated when selecting a target function from a plurality of different functions relating to radiographic image capturing;
   a controller that, when a first condition is established, in which a predetermined region of the electronic imaging cassette has been placed at a predetermined position, causes a function that renders control by operation with respect to the operation unit ineffective to be selected, and, when a second condition is established, in which the predetermined region is not placed at the predetermined position, causes a function that renders control by operation with respect to the operation unit effective to be selected; and
   an execution unit that, when the operation unit is operated, executes a function that the controller causes to be selected.

4. A radiographic imaging system comprising:
a portable radiographic imaging device that comprises an electronic imaging cassette having:
   an operation unit peripheral to an irradiating surface of the electronic imaging cassette, wherein the operation unit is configured to be operated when selecting a target function from a plurality of different functions relating to radiographic image capturing;
   a controller that, when a first condition is established, in which a predetermined region of the electronic imaging cassette has been placed at a predetermined position, causes a function associated with the first condition to be selectable via the operation unit, and, when a second condition is established, in which the predetermined region is not placed at the predetermined position, causes a function associated with the second condition to be selectable via the operation unit; and
   an execution unit that, when the operation unit is operated, executes a function that the controller causes to be selectable via the operating unit; and
a communication device that, when the first condition is established, causes the execution unit to execute the function associated with the second condition, by carrying out communication with the portable radiographic imaging device.

5. A radiographic imaging system comprising:
a portable radiographic imaging device that comprises an electronic imaging cassette having:
   an operation unit peripheral to an irradiating surface of the electronic imaging cassette, wherein the operation unit is configured to be operated when selecting a target function from a plurality of different functions relating to radiographic image capturing;
   a controller that, when a first condition is established, in which a predetermined region of the electronic imaging cassette has been placed at a predetermined position, causes a function that renders control by operation with respect to the operation unit ineffective to be selected, and, when a second condition is established, in which the predetermined region is not placed at the predetermined position, causes a function that renders control by operation with respect to the operation unit effective to be selected; and
   an execution unit that, when the operation unit is operated, executes a function that the controller causes to be selected; and
a communication device that, when the first condition is established, causes the execution unit to execute the function that renders control by operation with respect to the operation unit effective, by carrying out communication with the portable radiographic imaging device.

* * * * *